United States Patent [19]

Neubeck

[11] 4,180,917

[45] Jan. 1, 1980

[54] PROCESS FOR FREEZE-DRYING ENZYMES

[75] Inventor: Clifford E. Neubeck, Hatboro, Pa.

[73] Assignee: Rohm and Haas Company, Philadelphia, Pa.

[21] Appl. No.: 939,745

[22] Filed: Sep. 5, 1978

[51] Int. Cl.$^2$ .............................................. F26B 5/06
[52] U.S. Cl. ......................................................... 34/5
[58] Field of Search .......................................... 34/5, 92

[56] References Cited

U.S. PATENT DOCUMENTS 3,932,943  1/1976  Briggs et al. .............................. 34/5

Primary Examiner—John J. Camby

[57] ABSTRACT

This invention involves a novel process for freeze-drying enzymes.

11 Claims, No Drawings

PROCESS FOR FREEZE-DRYING ENZYMES

SUMMARY OF THE INVENTION

This invention relates to a novel process for the preparation of freeze-dried enzyme compositions. This process involves the steps of: (1) concentrating the enzyme solution by utilizing reverse osmosis or ultra-filtration; (2) addition of water-insoluble salts; (3) optional addition of inert suspenders and thickeners; and (4) freeze-drying this liquid enzyme concentrate.

BACKGROUND OF THE INVENTION

The use of organic solvent precipitation to obtain a suitable product has long been used in the baking, brewing and detergent industries. The physical properties of these organic solvent precipitated enzymes with respect to level of activity, stability, color, hygroscopicity, odor and caking are well-accepted in these industries.

The main problem with this process is that in the highly competitive low profit margin baking, brewing and detergent industries the use of organic solvent precipitation is an expensive operation since large volumes of solvent such as ethanol, isopropanol and the like are needed. Recovery operations and/or waste disposal of these large volumes of aqueous solvent filtrates further add to the expense of the operation.

Numerous attempts at freeze-drying enzymes have been reported in the literature. The main problems encountered in the past with the freeze-drying of enzymes has been an increase in the extent of denaturation with freeze-drying and the increase in instability, dark color, hygroscopicity, odor and caking compared with enzyme compositions obtained by the organic solvent precipitation of enzyme culture concentrates. The freeze drying of dialyzed enzyme solutions avoids many of these problems by removal of low molecular weight interfering salts and carbohydrates but such practice is generally confined to small scale experiments.

Attempts in the past to stabilize enzyme compositions have turned to the art of binding the enzymes via covalent bonding to suitable substrates prior to freeze-drying the enzyme composition. Such carrier bound enzymes are useful in enzymatic reactions wherein said carrier bound enzyme can be removed from the final product. However, these carrier bound enzymes are not useful in products wherein the enzyme is incorporated into the final product unless the carrier itself can be designed so as not to interfere with the use of the final product.

For example, carrier bound enzymes that are bound on glass or on various and sundry polymers could not be incorporated into the baking, brewing or detergent industry products wherein the enzyme itself becomes part of the product. This invention allows for the production of dry, flowable enzyme products by the use of reverse osmosis or ultrafiltration followed by the addition of necessary adjuvants and freeze-drying. This process produces dry concentrates having a physical appearance and shelf stability similar to the more expensive organic solvent precipitated counterparts.

The use of reverse osmosis or ultrafiltration is an essential part of this invention. There is no great distinction between reverse osmosis and ultrafiltration. Pressure is used in conjunction with semi-permeable membranes to effect separations. In practice, however, the separations achieved, and the operating conditions used are usually quite different.

Reverse osmosis membranes are generally considered to be those that are highly semi-permeable with respect to low-molecular weight solutes including salts such as sodium chloride. Ultrafiltration membranes have little or no permselectively for such solutes; — in fact, one of their important applications lies in the separation of colloids or macromolecules, which are retained by the membrane, from low molecular weight solutes which pass through.

Michael's (Ultrafiltration in Progress in Separation & Purification Vol. I E. S. Perry Ed. Interscience NY 1968 p. 297) suggested that the separation of solutes whose molecular dimensions are within one order of magnitude of that of the solvent be called reverse osmosis, and that the term ultrafiltration be used to describe separations between solutes having dimensions greater than 10 solvent diameters but less than the resolution of the optical microscope (ca 0.5 $\mu$).

An alternate arbitrary differentiation is that in reverse osmosis there is usually a significant osmotic pressure to overcome. In reverse osmosis the osmosis is usually carried out at high pressure, approximately 50 atmospheres, while ultrafiltration is performed at low pressure, less than 5 atmospheres.

These techniques not only concentrate the liquid enzyme solution, but in the process, remove a substantial quantity of lower molecular weight materials such as inorganic salts and low molecular weight carbohydrates and peptides. These materials tend to degrade the physical appearance of the final dried product by causing discoloration, odor, hygroscopicity and instability.

DETAILED DESCRIPTION OF THE INVENTION

The process of this invention relates to the preparation of a freeze-dried enzyme composition wherein the liquid enzyme solution is first concentrated by the use of ultrafiltration or reverse osmosis techniques. To this liquid enzyme solution concentrate is then added water-insoluble salts.

These salts perform two functions. First, they must be selected via their insolubility so that the freezing point of the liquid enzyme concentrate is not significantly lowered. Second, they must be selected so that they form a non-settling suspension which allows for faster, more uniform freeze drying of the solution. The water insoluble salts can be formed in the liquid enzyme concentrate by adding sequentially two or more soluble salts which form an insoluble precipitate in the enzyme solution. Additional non-settling adjuvants can also be added to the liquid enzyme concentrate depending upon the ultimate use of the final enzyme product and the difficulty of obtaining a suitable non-settling suspension.

Finally, this liquid enzyme concentrate, which contains water-insoluble salts and, optionally, thickeners and suspenders, is freeze-dried at temperatures from about −78° C. to about 0° C. in vacuo. The vacuum is supplied by mechanical vacuum pumps and the enzyme concentrate is subjected to the conditions of low temperature and pressure until a major part of the water is removed by sublimation. Heat is optionally applied to hasten the sublimation. The resulting material is then ground and sieved to obtain a free-flowing, non-caking product.

A preferred process of this invention is the use of the above process for the preparation of freeze-dried protease compositions and freeze-dried alpha-amylase compositions derived from fungal and bacterial cultures for use in the food, brewing and detergent industries, more preferably in the baking industry.

The following examples are presented to illustrate the process encompassed by the present invention. These examples are presented merely as illustrations of this process and are not meant to be considered in any way as limitations on the breadth and scope of the present invention.

EXAMPLE I

A selected strain of *Bacillus subtilis* was grown on 15,000 pounds of medium containing corn hominy, cornstarch and soybean meal under deep tank conditions to produce a culture exhibiting a protease activity of 1540 casein solubilizing units (EE)*. Bacterial cells and medium debris were removed by filtration on a rotary vacuum filter using diatomaceous earth as a filter aid. The clear culture filtrate plus wash amounted to 17,000 pounds at an activity of 1,004 EE (activity recovery=74%).

*Casein solubilizing units (EE) may be defined as follows: An enzyme with an activity of 1000 casein solubilizing units (EE) solubilizes nine times its weight of casein in one hour at 40° C. and pH 8.0.

The culture filtrate plus wash was concentrated to an activity of 8,300 EE in an ultrafiltration unit operating at 10° C.±5° C. An aliquot of this partial concentrate (5.39×activity of the crude culture) was removed for freeze drying. The concentration was continued until the final concentrate activity was 22,500 EE (14.6×activity of crude culture).

Each of the concentrates was treated with a mixture of diammonium and monoammonium phosphates plus calcium carbonate. The ammonium phosphates were added in four increments to minimize a change in pH. Finally, the calcium carbonate necessary to form waste insoluble calcium phosphate was added. Carbon dioxide was evolved and a stable frothy gel was obtained when the mixture containing the 14.6×concentrate was held for 20 hours at 5° C. A gel was also formed in the case of the 5.39×concentrate but some separation of the insoluble calcium phosphate was obtained and the frozen mass was not as homogenous as the 14.6×concentrate.

The frozen concentrate is then placed in a freeze drier, evacuated to 1,200 microns and heat is applied. The temperature of the product at the beginning of the process is −1° C. After one hour the temperature reaches −10° C. and it finally equilibrates at 24° C. over the next 17 hours. The product is then ground and sieved.

Table I summarizes the data from two experiments pertaining to the freeze drying of the concentrates. Excellent quality products comparable to the dry product prepared by organic solvent precipitation (isopropyl alcohol) were obtained. The recovery of activity in the freeze dried product was better than the routinely obtained (60–65%) using cold (5°–10° C.) isopropyl alcohol to precipitate the enzyme followed by drying in a current of air at 50° C.

The bacterial proteases so prepared can be used for cracker dough modification and protein hydrolyzate preparations.

TABLE I

Freeze-Drying of *Bacillus subtilis* Concentrated Filtrate Treated With $(NH_4)_2HPO_4$, $NH_4H_2PO_4$ and $CaCO_3$

|  | Test A - Concentrate at 5.39 × Culture Activity | Test B - Concentrate at 14.6 × Culture Activity |
|---|---|---|
| Concentrate Activity (EE) | 8,300 | 22,500 |
| % $(NH_4)_2HPO_4$ Added W/W | 5.1 | 10 |
| % $NH_4H_2PO_4$ Added W/W | 5.1 | 10 |
| % $CaCO_3$ Added W/W | 12.3 | 23 |
| Weight of Concentrate (Pounds) | 5.60 | 1.61 |
| Weight of Treated Concentrate (Pounds) | 6.86 | 2.32 |
| Activity of Treated Concentrate (EE) | 6,860 | 16,00 |
| Weight of Freeze-Dried Product (Pounds) | 1.97 | 0.97 |
| Activity of Freeze-Dried Product (EE) | 21,600 | 27,000 |
| Physical Appearance | Good, but not uniform. | Excellent, white and dry. Easily ground. |
| Recovery of Activity - Calculated based upon activity of concentrate vs. treated concentrate | 101% | 102% |
| Recovery of Activity - Calculated based upon activity of treated concentrate vs. freeze dried product | 90.4 | 72.4 |
| Recovery of Activity Overall - Calculated based upon activity of concentrate vs. freeze dried product | 91.3 | 74.2 |
| Vacuum - 1200 microns absolute at time zero; 200 microns absolute at time 6 to 19 hours. |  |  |
| Maximum Temperature (product exposed to) | −10° C. <br> −°C. <br> 24° C. | time zero <br> 1 hour <br> 2–19 hours |

EXAMPLE II

Using a process analogous to that shown in Example I the following bacterial protease was also prepared.

A selected strain of *Bacillus subtilis* was grown on 42,000 pounds of medium containing hominy, cornstarch and soybean under deep tank conditions to produce a culture at 3,800 EE proteolytic activity. After filtration and washing 61,000 pounds of clear filtrate at 2,480 EE was obtained.

The culture filtrate was concentrated by ultrafiltration to an activity of 20,000 EE. Diammonium phosphate at 5.7% W/W, calcium acetate at 7.0% W/W and cornstarch at 5.0% W/W were added in sequence with good mixing. The mixture remained fluid but the precipitated calcium phosphate and starch remained suspended. The mixture was freeze dried according to the procedure of Example I to produce a light tan colored solid having 52,000 EE. Recovery of activity was 83.5%.

EXAMPLE III

A selected strain of *Aspergillus oryzae* was grown under deep tank conditions on a medium containing a mixture of liver, soybean, and blood meals to produce a culture (48,000 pounds) showing an activity of 8,800 HU*. Fungal mycelium and culture debris were removed by filtration on a rotary vacuum filter using diatomaceous earth as a filter aid. The clear filtrate plus wash (64,760 pounds) had an activity of 6,520 HU. (Recovery 100%).

*HU—An enzyme has an activity of 1,000 HU per g if 11.18 mg. of it produces an increase in soluble nitrogen of 5.0 mg. from 0.417 g hemoglobin in 5 hours at 40° C. and pH 4.7.

The culture filtrate plus wash was concentrated to an activity of 240,000 HU but the concentrate exhibited deterioration to 208,000 HU before treatment and freeze drying.

Seventy pounds (27% W/W) of cornstarch was added to 258 pounds of *A. oryzae* protease concentrate, 208,000 HU, at 10° C. After a smooth mixture was obtained, 23 pounds (9%) calcium acetate was added with good mixing. The mixture showed good suspension of the starch and the insoluble calcium phosphate resulting from the mixing of the calcium acetate and the residual phosphate already present in the protease concentrate. The concentrate, after addition of calcium acetate and starch had an activity of 135,000 HU. The test showed the following recovery of activity:

| Recovery Activity | |
|---|---|
| Step 1 - After mixing with Ca(OAc)₂ and starch | 88% |
| Step 2 - After Freeze-Drying | 99% |
| Overall Recovery | 87% |

The final product, after grinding and screening, had an activity of 283,000 HU. Approximately 105 pounds of fine product (>80 mesh) was produced from the 160 pounds total freeze dried product. The final product can be used for dough modification by blending or tableting.

Table II

Utilizing the procedures described in Example III the following tests were performed Freeze-Drying *Asperigillus oryzae* Protease Concentrated Filtrate

| | Test A | Test B | Test C | Test D | Test E |
|---|---|---|---|---|---|
| Activity of Conc. (HU) | 160,000 | 160,000 | 160,000 | 160,000 | 160,000 |
| % Starch Added W/W | 22.5 | 24.75 | 24.75 | 27.0 | 27.0 |
| % Ca(OAc)₂ Added | 7.5 | 8.25 | 8.25 | 9.0 | 9.0 |
| Wt. Concentrate-(lbs.) | 10.82 | 15.47 | 3.25 | 17.0 | 4.41 |
| Wt. Treated Conc.-(lbs.) | 14.07 | 20.63 | 4.34 | 25.00 | 6.48 |
| Activity Treated Conc. (HU) | 102,000 | 95,600 | 95,600 | 95,600 | 95,600 |
| Suspension of Insol. | Good | Very Good | Very Good | Very Good | Very Good |
| Wt. Freeze-Dried Prod. (lbs) | 6.26 | 9.82 | 1.94 | 10.55 | 2.97 |
| Activity Freeze-Dried Product (HU) | 238,000 | 206,000 | 219,000 | 193,000 | 212,000 |
| Physical Appearance | Light Brown Easily Ground | | | | |
| Recovery Activity | | | | | |
| Conc. to Treated | 83% | 80% | 80% | 88% | 88% |
| Treated to Dry | 104% | 103% | 102% | 85% | 102% |
| Overall | 86% | 81% | 82% | 75% | 89% |
| Time to Dry | 20 Hr. | 17.5 Hr. | 21.5 Hr. | 18.5 Hr. | 21 Hr. |
| Max. Temp. Product Exposed to | 88° F. | 85° F. | 80° F. | 85° F. | 80° F. |

Obtained 31.54 lbs. from combined batches. After grinding and screening obtained 29 pounds. After ball milling obtained 22 lbs. screened through 80 mesh plus 6 lbs. of screenings having an activity of 200,000 HU.

EXAMPLE IV

A strain of *Bacillus subtilis* selected to produce amylase was grown on 15,000 pounds of medium containing cornstarch, corn steep water and inorganic salts under deep tank conditions to produce a culture having 20,000 starch liquifying units*. After filtration and washing 17,000 lbs. of filtrate was obtained having 15,000 starch liquifying units.

*An enzyme with 1000 starch liquifying units per g reduces the viscosity of 300 times its weight of potato starch by 90% in 10 minutes at 70° C. and pH 6.7.

The culture filtrate was concentrated to an activity of 51,000 starch liquifying units. Diammonium phosphate at 8.2% W/W, calcium acetate at 4.5% W/W and cornstarch at 9.0% W/W were added in sequence with good mixing. After drying, a product 130,000 starch liquifying units activity was obtained. The activity yield was 96.6%.

The following Table III illustrates how the variation in additives affected the quality, activity and recovery of activity in the dried product.

TABLE III

| Level of Additives $(NH_4)_2HPO_4$ | $Ca(OAc)_2$ | Starch | Quality of Dry Product | Activity[a] | % Yield[b] |
|---|---|---|---|---|---|
| 0 | 0 | 0 | very dark | — | — |
| 6.8 | 3.7 | 16 | hard, tan | — | — |
| 6.8 | 3.7 | 7.5 | hard, dark, gummy | — | — |
| 8.2 | 4.5 | 9.0 | soft tan | 130,000 | 96.6 |
| 11.0 | 6.0 | 12.0 | very soft, light tan | 105,000 | 89.6 |
| 11.0 | 6.0 | 8.0 | very soft, light tan | 120,000 | 94.5 |
| 11.0 | 6.0 | 16.0 | very soft, light tan | 99,500 | 91.8 |
| 8.2 | 4.5 | 16.0 | slightly hard, light tan | 108,000 | 94.9 |

[a] Activity in Liquifying Units
[b] % Yield of Activity Recovered

Tables IV and V present a summary of laboratory vacuum drying tests at 30° C. on *Aspergillus oryzae* protease concentrate plus admixes. These small scale tests could be correlated to the large freeze drying process and therefore they were first run in order to determine the best ratios of additives for study in the freeze drying process.

*Aspergillus oryzae* concentrate, 30 Brix and 160,000 HU is treated with additives as noted and dried in vacuo at 30° C. The additives and the percentages used are given in Table IV. The HU activity, recovery, and visual appearances are given in Table V.

TABLE IV

| Test No. | $NH_4H_2PO_4$ | $(NH_4)_2HPO_4$ | $Ca(OAc)_2$ | $CaCO_3$ | $Ca_3(PO_4)_2$ | Starch | Other |
|---|---|---|---|---|---|---|---|
| 1 | — | — | — | — | — | — | — |
| 2 | 6.25 | 1.25 | 12.5 | — | — | — | — |
| 3 | 12.5 | 2.5 | 25 | — | — | — | — |
| 4 | 12.5 | 2.5 | — | 25 | — | — | — |
| 5 | — | — | — | 25 | — | — | — |
| 6 | — | — | 25 | — | — | — | — |
| 7 | — | — | — | 12.5 | — | 12.5 | — |
| 8 | — | — | 12.5 | — | — | 18.5 | — |
| 9 | — | — | — | — | — | 25.0 | — |
| 10 | — | — | — | — | — | 18.8 | — |
| 11 | — | — | 12.5 | — | — | 12.5 | — |
| 12 | — | — | 12.5 | — | — | — | Flour 12.5 |
| 13 | — | — | 6.25 | — | — | 18.8 | — |
| 14 | — | — | 6.25 | — | — | 18.8 | — |
| 15 | — | — | 6.25 | — | — | — | Dextrin 18.8 |
| 16 | — | — | 2.5 | — | — | 22.5 | — |
| 17 | — | — | 7.5 | — | — | 12.5 | — |
| 18 | — | — | 7.5 | — | — | 18.8 | — |
| 19 | — | — | 7.5 | — | — | 22.5 | — |
| 20 | — | — | 10.0 | — | — | 12.5 | — |
| 21 | — | — | 10.0 | — | — | 18.8 | — |
| 22 | — | — | 10.0 | — | — | 22.5 | — |
| 23 | — | — | 12.5 | — | — | 12.5 | — |
| 24 | — | — | 12.5 | — | — | 18.8 | — |
| 25 | — | — | 12.5 | — | — | 22.5 | — |
| 26 | — | — | — | — | 6.25 | — | — |
| 27 | — | — | — | — | 12.50 | — | — |
| 28 | — | — | — | — | 25.0 | — | — |
| 29 | — | — | — | — | — | — | Gelatinized Starch 6.25 |
| 30 | — | — | — | — | — | — | 12.5 |
| 31 | — | — | — | — | — | — | 25.0 |

TABLE V

| Test No. | Appearance | HU | Activity Recovery |
|---|---|---|---|
| 1 | Wet, dark | ND | ND |
| 2 | Dark, gummy | 283,000 | 75 |
| 3 | Dry, white friable | 175,000 | 58 ± 1 |
| 4 | Dry, light | 219,000 | 88 |
| 5 | brown, gummy Wet, dark | ND | ND |
| 6 | Damp, light friable | 260,000 | 81 ± 9 |
| 7 | Wet, dark | ND | ND |
| 8 | Dry, light friable | 264,000 | 88 |
| 9 | Dark, hard | ND | ND |
| 10 | Dark, hard | ND | ND |
| 11 | Dark, hard | 260,000 | 85 |
| 12 | Dark, hard | ND | ND |
| 13 | Light, friable | 264,000 | 81 |
| 14 | Light, friable | 264,000 | 82 |
| 15 | Dark, hard | ND | ND |
| 16 | Dark, hard | 260,000 | 81 |
| 17 | Dry, light, friable | 280,000 | 81 |
| 18 | Dry light, friable | 264,000 | 86 |
| 19 | Dry light, | 270,000 | 93.5 ± 1.5 |

TABLE V-continued

| Test No. | Appearance | HU | Activity Recovery |
|---|---|---|---|
| | friable | | |
| 20 | Dry, dark, friable | 250,000 | 76 |
| 21 | Dry, Light brown Friable | 230,000 | 78 |
| 22 | Dry, light, friable | 220,000 | 70 |
| 23 | Dark | 230,000 | 70 |
| 24 | Dark | 219,000 | 77 |
| 25 | Dark | 208,000 | 78 |
| 26 | Dark | 410,000 | 87 |
| 27 | Dark | 320,000 | 80 |
| 28 | Light | 246,000 | 77 |
| 29 | Dark gum | 338,000 | 69 |
| 30 | Dark gum | 293,000 | 81 |
| 31 | Dark gum | 202,000 | 88 |

As can be seen from the above data the concentrate wherein calcium acetate and starch were utilized gave the best results as far as good appearance and recovery of activity are concerned. See examples 8, 13, 14, 17, 18, 19, 21, 22 and 28.

The freeze-dried enzyme composition prepared by the process of the present invention can be utilized in the food, brewing, detergent and leather industries and suitable carriers for such use can be incorporated therein. The incorporation of such carriers into these formulations are well known to the artisan in the field and such obvious extensions of the process of the present invention are meant to be encompassed by the spirit and scope of this invention.

The use of the freeze-dried enzyme compositions prepared by the process of the present invention are particularly useful in the baking and brewing industries where there is a need for a highly concentrated, dry, flowable, light colored, odorless, non-hygroscopic GRAS product with good stability.

I claim:

1. A process for the preparation of freeze-dried enzyme compositions which comprises: concentrating a liquid enzyme solution by ultrafiltration; adding to said concentrate water-insoluble salts, and optionally suspenders and thickeners, to obtain a non-settling concentrate composition, and freeze-drying said concentrate composition at temperatures from about −78° C. to about 30° C. in vacuo.

2. A process according to claim 1 wherein the water insoluble salts are selected from the group consisting of tribasic calcium phosphate, tribasic magnesium phosphate, calcium ammonium phosphate, calcium hypophosphate, calcium magnesium silicate, calcium silicate, calcium sulfite, calcium tartarate, magnesium oxide and magnesium silicate.

3. A process according to claim 2 wherein the water insoluble salt is tribasic calcium phosphate.

4. A process according to claim 3 wherein the water insoluble salt is formed in situ by the reaction of a water soluble phosphate salt and a water soluble calcium salt.

5. A process according to claim 4 wherein the water soluble phosphate salts and water soluble calcium salts are added until a gel is formed.

6. A process according to claim 5 wherein the water soluble phosphate salt is selected from the group consisting of sodium potassium and ammonium phosphates or mixtures thereof and the water soluble calcium salt is selected from the group consisting of acetate, carbonate, chloride, hydroxide and sulfate or mixtures thereof.

7. A process according to claim 3 wherein tribasic calcium phosphate is added to the liquid enzyme solution concentrate until a gel is formed.

8. A process according to claim 4 wherein suspenders and thickeners are added which are selected from the group consisting of cornstarch, locust bean gum, carib, xanthan gum, and gum arabic.

9. A process according to claim 6 wherein the enzyme is a protease derived from a Bacillus sps.

10. A process according to claim 6 wherein the enzyme is a protease derived from an Aspergillus sps.

11. A process according to claim 6 wherein the enzyme is an amylase derived from a Bacillus sps.

* * * * *